United States Patent [19]

Ito et al.

[11] Plant 4,069

[45] July 5, 1977

[54] RUBBER PLANT (FICUS GOLD KING)

[75] Inventors: Tokuyasu Ito; Hideo Ikuta, both of Hekinan, Japan

[73] Assignee: Cerro Gordo, Inc., Vega Alta, P.R.

[21] Appl. No.: 713,994

[22] Filed: Aug. 12, 1976

[30] Foreign Application Priority Data

Aug. 19, 1975 Japan ..... 50-99798

[51] Int. Cl.[2] ..... A01H 5/12

[52] U.S. Cl. ..... Plt./88

[58] Field of Search ..... Plt./88

*Primary Examiner*—Robert E. Bagwill

*Attorney, Agent, or Firm*—J. Gibson Semmes

[57] ABSTRACT

A rubber plant exhibiting variegated foliage and resembling the known *Ficus elastica* Roxb. var. *decora* tricolor hort., but bearing leaves exhibiting very narrow dark-green borders and light-yellow interiors and being smaller in size. The leaf blades are of an ovate shape with a thick coriaceous texture and with wavy edges. Propagation of the rubber plant by using cuttings is difficult and even impossible, therefore, air layering is employed.

8 Drawing Figures

This invention relates to a new and distinct variety of a rubber plant having border-variegated foliage, *Ficus elastica* Roxb. var. *decora* tricolor hort., which variety is characterized particularly by its leaf blades exhibiting narrow dark-green borders and light-yellow interiors.

This new variety of rubber plant was discovered Oct. 5, 1972 as a bud mutation in one of the specimens while we were cultivating approximately 500 plants of another new variety of rubber plant having border-variegated foliage, *Ficus elastica* Roxb. var *decora* tricolor hort., at a greenhouse of Mr. Tokuyasu Ito, one of the inventors, located at No. 56, 6-chome, Kamiaricho, Hekinan-shi, Aichi-ken, Japan. The latter new variety of rubber plant with border-variegated foliage was discovered on July 10, 1971 as a bud mutation while we were cultivating approximately 5,000 plants of a known variety of rubber plant, *Ficus elastica* Roxb. var. *decora* tricolor hort., at the greenhouse of Mr. Tokuyasu Ito located at the same place. This plant of the known variety was first imported from West Germany to Japan around 1960 and propagated by Mr. Diazo Oguri residing at Iwasuberi-cho, Handa-shi, Aichi-ken, Japan. Some of the propagated plants were transferred to Mr. Ito and propagated by us since the summer of 1962. Ever since the finding of this new variety in 1971, we have propagated the new variety with leaf blades exhibiting border variegations by stem-cutting (single eye cutting). It has been confirmed that the characteristics of this new variety with leaf blades exhibiting border variegations are very uniform and stable in respective specimens. The plant patent application for this new variety of rubber plant with leaf blades exhibiting border variegations was filed on the same day as the present plant patent application.

Ever since the finding of this new variety of the present invention in 1972, we have propagated this new variety of rubber plant having leaf blades exhibiting narrow dark-green borders and light-yellow interiors by the air layering process. It has been confirmed that the characteristics of this new variety are very uniform and stable in respective specimens.

COMPARISONS OF CHARACTERISTICS AMONG (1) A SPECIMEN SEPARATED FROM THE 1971-DISCOVERED PARENT PLANT EXHIBITING BORDER VARIEGATIONS, (2) THE 1972-DISCOVERED PARENT PLANT OF THE NEW VARIETY OF THE PRESENT INVENTION AND (3) A SPECIMEN OF THE NEW VARIETY OF THE PRESENT INVENTION SEPARATED FROM THE 1972-DISCOVERED PARENT PLANT

1. Characteristics of a specimen separated from the 1971-discovered parent variety exhibiting border variegations.

The specimen of the 1971-discovered parent plant is, as set forth hereinbefore, a bud mutation of the known variety, *Ficus elastica* Roxb. var. *decora* tricolor hort., the application of said specimen of the 1971-discovered parent variety was filed on the same day as the present application. Said specimen of the 1971-discovered parent plant is characterized over the known rubber plant having variegated foliage, *Ficus elastica* Roxb. var. *decora* tricolor hort., in that proportions of light yellow areas of the variegated leaves are small as a whole, said light-yellow areas appearing relatively narrow in size and are distinctly located on the edges of the leaves to form a so-called "thread-like border variegation"; leaves before development, namely buds and young leaves are reddish in color; grown leaves are larger in size than leaves of the known *Ficus elastica*

Figure 3:
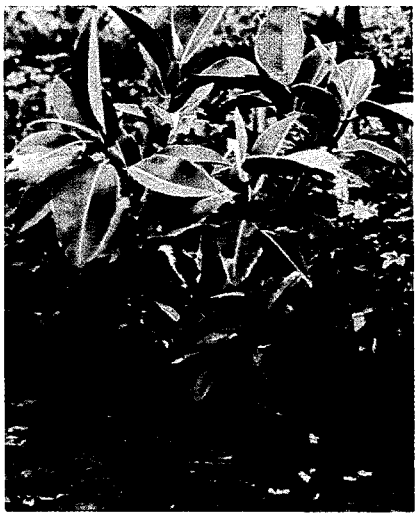
FIG. 3 is a view of the 1971-discovered parent plant exhibiting border variegations.
Figure 4A:
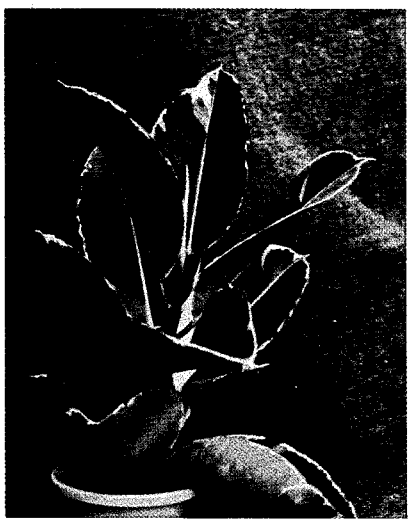
FIGS. 4A and 4B are views of a typical specimen separated from the 1971-discovered parent plant and a grown leaf of said specimen, respectively.
Figure 4B:
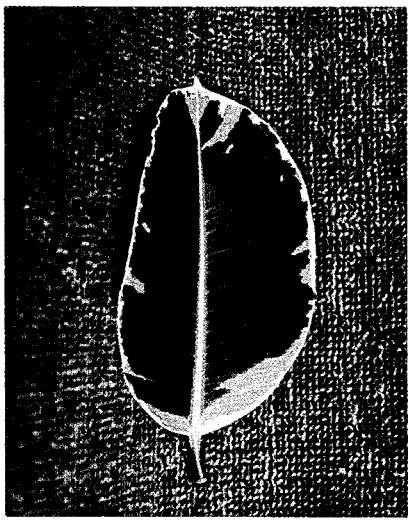

Roxb. var. *decora* tricolor hort. and have an oblong shape with a thick coriaceous texture; and the specimen of the 1971-discovered parent plant can be easily propagated by stem-cutting (single eye cutting) (see FIGS. 3, 4A and 4B).

2. Characteristics of the 1972-discovered parent plant of the new variety of the invention.

Figure 1:
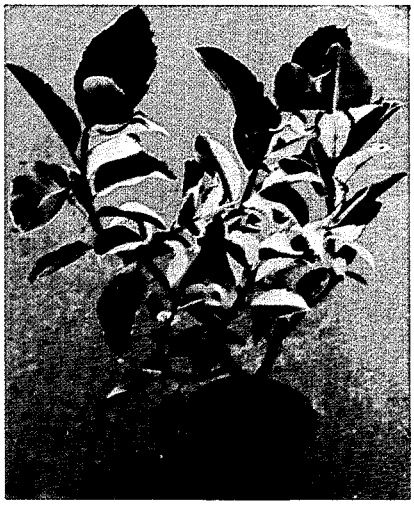
FIG. 1 is a view of the 1972-discovered parent plant of the new variety of the invention.

The parent plant of the new variety of this invention is, as set forth hereinbefore, a bud mutation of the above-mentioned 1971-discovered variety characterized as having leaf blades of a so-called thread-like border variegation as shown in FIGS. 4A and 4B and having reddish buds and reddish young leaves. The characteristics of the parent plant of the new variety of this inventon are still being maintained and preserved in the original potted parent plant (see FIG. 1) since its discovery in 1972. The varied branches of the 1972-discovered parent plant are still forming leaves with blades exhibiting narrow dark-green borders and light-yellow interiors while other branches are forming leaves with blades exhibiting the above-mentioned thread-like border variegations. Namely, both types of branches producing leaves of the wide interior variegations and of branches producing leaves of the narrow border variegations are co-present in the parent plant (see FIG. 1).

Growth is vigorous in branches producing leaves of the thread-like border variegation but the branches producing leaves of the narrow dark-green border and light-yellow interior variegations show less vigorous growth.

Formation of light-yellow interior in the leaf blade is stable, and this variegation is substantially uniform throughout all of the leaves showing said variegations.

Leaves: blades of the grown wide light-yellow interior variegated leaves about 22 centimeters long and about 13 centimeters wide at its widest length; their petioles about 3.5 centimeters long. The grown light-yellow interior variegated leaves of the 1972-discovered parent plant are somewhat larger than those of the specimens separated from said parent plant for cultivation. The reason being considered to be that nutrients are well absorbed by the parent plant, because said parent plant has in addition to the light-yellow interior variegated leaves, leaves with the light-yellow borders.

What is most interesting is that, while specimens separated from the narrow light-yellow border leaf branches of the parent tree are cultivated in a greenhouse under the following conditions, varied plants having leaf blades exhibiting narrow dark-green borders and light-yellow interiors appear at an average rate of one plant per approximately 500 specimens. The cultivation conditions are such that the greenhouse is warmed at about 7° to 10° C in the winter, namely from November to the beginning of March, but not warmed during spring and autumn, and is shaded from the sun by placing a black Victorian lawn on the top part of the greenhouse during summer, namely from the end of May to the beginning of October.

3. Characteristics of a specimen of the new variety separated from the 1972-discovered parent plant.

Figure 5A:
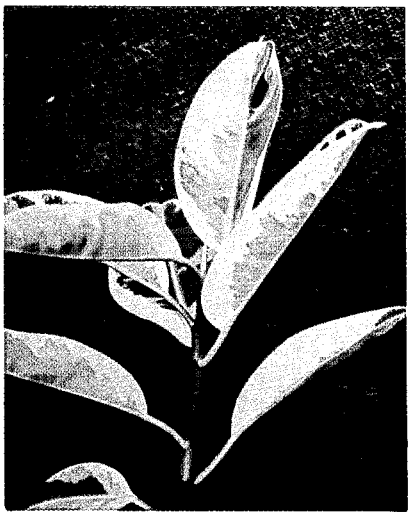
FIGS. 5A and 5B are views of a known variety of rubber plant, *Ficus elastica* Roxb. var. *decora* tricolor hort., and its grown leaf, respectively.
Figure 5B:
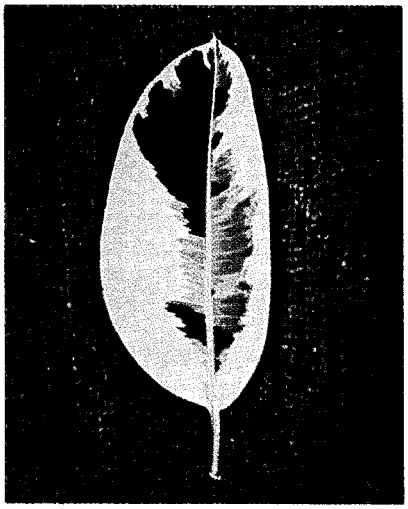

As compared with the known variety, *Ficus elastica* Roxb. var. *decora* tricolor hort., shown in FIGS. 5A and 5B, with the new variety (shown in FIGS. 3, 4A and 4B) separated from the 1971-discovered parent plant with leaf blades of narrow light-yellow border variegation, and with the 1972-discovered parent plant (shown in FIG. 1) of the new variety of the invention, the new variety of this inventon shows a low rate of growth and very short internode length. The internode length is about ⅓ of that in the known *Ficus elastica* tricolor variety.

Leaves: somewhat smaller in size than those of the known *Ficus elastica* tricolor variety, leaf blades, about 14 to 15 centimeters long, about 9 to 10 centimeters wide, ovate in shape and thick coriaceous texture, with wavy peripheral edges. Petioles about 3 centimeters long.

Figure 2A:
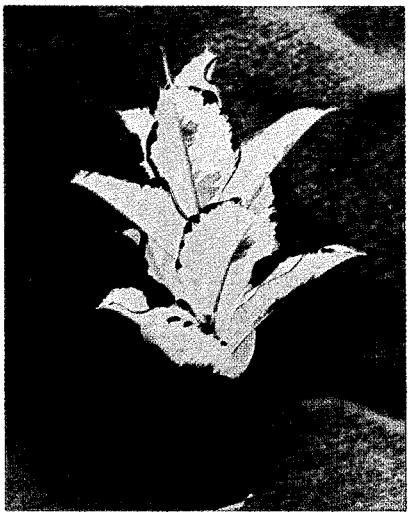
FIGS. 2A and 2B are views of a typical specimen of the new variety of the invention separated from the 1972-discovered parent plant, and a grown leaf of said specimen, respectively.
Figure 2B:
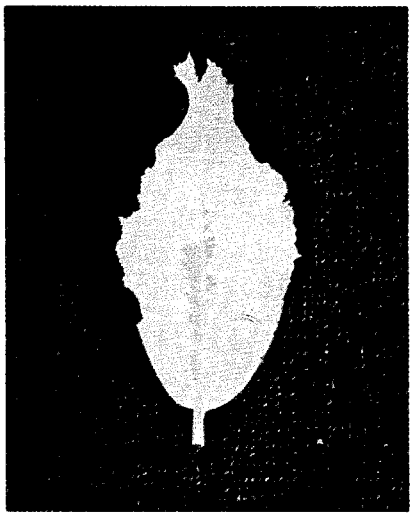

As shown in FIGS. 2A and 2B, chloroplast substantially disappears at the interior of the leaf blades while a very narrow dark-green area having a width of about one centimeter is left along the edge of the leaf blade. The dark-green area narrows toward the leaf tip. Chloroplast is absent in the leaf base portion, and the boundary between the dark-green area and the light-yellow interior area is very distinct.

Distance between two adjacent leaves, namely the internode length, is very short and about ⅓ of that in the known *Ficus elastica* tricolor variety. Grown leaves exhibiting the beautiful narrow dark-green borders and light-yellow interiors mentioned above do not readily fall off. Accordingly, the new variety is a foliage plant particularly suitable for potting.

Propagation: Propagation of the rubber plant of the new variety by using cuttings is difficult and even impossible. The reason being that the size of the dark-green area is very small. Propagation is accordingly possible only by layering. Thus, the propagation rate is low, and the new variety has a high value due to its rarity.

What we claim is:

1. A new and distinct variety of *Ficus elastica* Roxb. var. *decora* tricolor hort., substantially as herein shown and described, characterized over the known rubber plant having variegated foliage, *Ficus elastica* Roxb. var. *decora* tricolor hort., in that leaves are smaller in size, the leaf blade has an ovate shape with a thick coriaceous texture and exhibits a very narrow dark-green area appearing on the edge of the leaf blade and a light-yellow area appearing at the interior of the leaf blade, the boundary between the dark-green border area and the light-yellow interior area is very distinct; the peripheral edge of the leaf blade is wavy; the internode length is shorter; the rate of growth is lower and, since propagation by using cuttings is difficult, air layering is employed.

* * * * *